Figure 1:
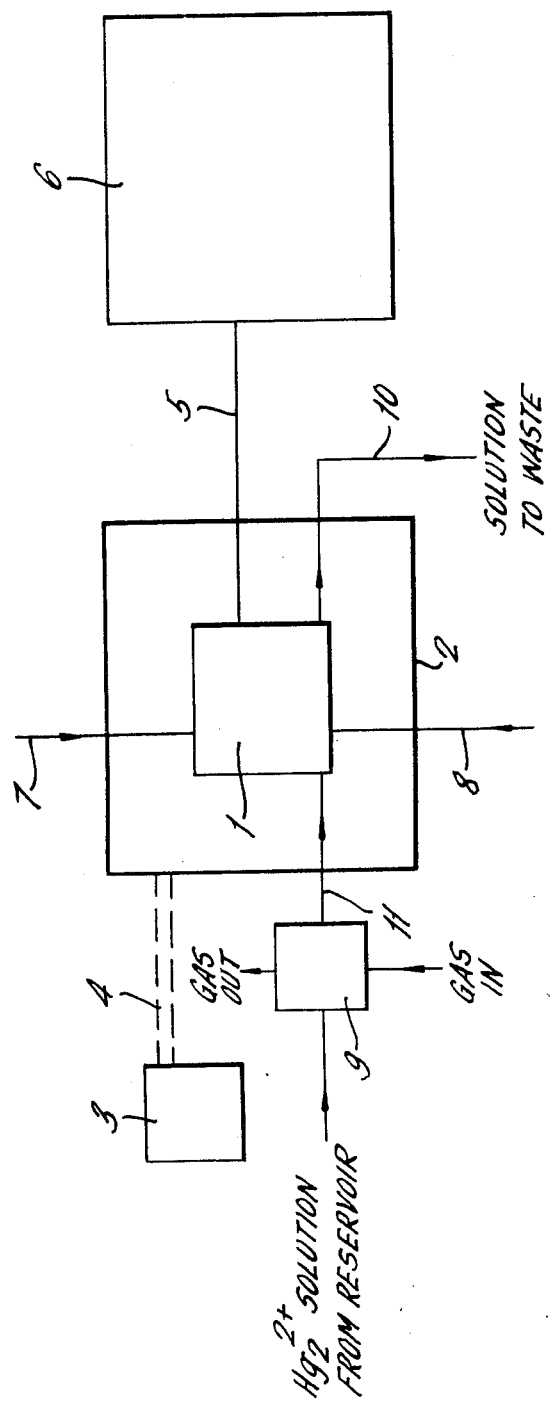

United States Patent [19]

Marshall et al.

[11] 4,404,287
[45] Sep. 13, 1983

[54] METHOD AND APPARATUS FOR DETERMINING CHEMICAL SPECIES

[75] Inventors: Geoffrey B. Marshall, Chessington; Derek Midgley, Ashtead, both of England

[73] Assignee: Central Electricity Generating Board of Sudbury House, London, England

[21] Appl. No.: 210,438

[22] Filed: Nov. 25, 1980

[51] Int. Cl.³ .................... G01N 27/66; G01N 33/00
[52] U.S. Cl. .................... 436/109; 436/111; 436/122; 436/129
[58] Field of Search ............ 23/23 R, 23 PC, 232 R, 23/232 E; 436/119, 122, 129, 109, 111

[56] References Cited

U.S. PATENT DOCUMENTS

| | | | |
|---|---|---|---|
| 2,648,598 | 8/1953 | Stitt et al. | 23/232 R |
| 3,704,097 | 11/1972 | Capuano | 23/230 PC |
| 3,826,614 | 7/1974 | Capuano | 222/78 |
| 3,826,616 | 7/1974 | Capuano | 23/230 PC |
| 3,844,719 | 10/1974 | Hammitt | 422/78 |
| 3,884,639 | 5/1975 | Sugigama | 23/230 PC |
| 4,023,929 | 5/1977 | Becker et al. | 23/230 PC |
| 4,138,215 | 2/1979 | Huber | 422/116 |
| 4,208,372 | 6/1980 | Huber | 422/81 |
| 4,271,125 | 6/1981 | Leichnitz | 23/232 R |

FOREIGN PATENT DOCUMENTS

| | | |
|---|---|---|
| 1364974 | 8/1974 | United Kingdom . |
| 1520870 | 8/1978 | United Kingdom . |
| 1542155 | 3/1979 | United Kingdom . |
| 2041518 | 9/1980 | United Kingdom .................. 422/83 |

OTHER PUBLICATIONS

Reactions of Trethylin Hydride with Inorganic Halides and Oxides; J.A.C.S. 9-20-57, vol. 79, pp. 4913–4915.
Moeller–Inorganic Chemistry, 1952, pp. 300, 852–855.
Dräger–Detector Tube Handbook; 4th ed., 1979, p. 36.
Chem. Abstr. 85:171267b
Chem. Abstr. 58:20a.

Primary Examiner—Michael S. Marcus
Attorney, Agent, or Firm—Beveridge, DeGrandi & Kline

[57] ABSTRACT

A method for the quantitative determination of a chemical species capable of promoting the disproportionation of $Hg_2^{2+}$ to $Hg^{2+}$ and $Hg°$ in solution which method comprises causing the species to react with a solution comprising $Hg_2^{2+}$ to thereby produce a measurable concentration of $Hg°$ in a gaseous phase above the solution, and determining the $Hg°$ present in the said gaseous phase.

The method is particularly applicable to the determination of low concentrations (e.g. as low as 0.1 p.p.b.) of $SO_2$ in gas mixtures, such as air.

8 Claims, 3 Drawing Figures

METHOD AND APPARATUS FOR DETERMINING CHEMICAL SPECIES

This invention relates to the quantitative determination of chemical species capable of promoting the disproportionation of mercurous ions in solution to mercuric ions and mercury metal.

In solution, the mercurous ion disproportionates according to the reaction:

$$Hg_2^{2+} \rightleftharpoons Hg^{2+} + Hg^\circ \qquad (1)$$

The reaction is reversible, and hence the equilibrium constant $K_d$ may be defined as:

$$K_d = \frac{[Hg^{2+}][Hg^o]}{[Hg_2^{2+}]}$$

Thus, reaction 1 is forced to the right by the addition of a species which will remove free mercury (II) ions from solution (e.g. a species which forms stronger complexes with mercury (II) ions than with mercury (I) ions, such that the equilibrium:

$$Hg^{2+} + nR \rightleftharpoons HgR_n^{2+} \qquad (2)$$

wherein R represents the complex-forming species, lies towards the right. This may be quantified by the equilibrium constant $\beta$, defined as $$\beta = \frac{[HgR_n]}{[Hg^{2+}][R]^n}$$

and suitable species R are those for which $\beta$ has a large value. It should of course be appreciated that the charge on the species $HgR_n$ may be other than $2+$, and indeed may be negative, depending on the charge if any on the species (R).

Thus, the addition of such a species which will promote the disproportionation of the mercurous ion to mercuric and mercury metal will give rise to free mercury metal, and this can be partitioned between the solution, and the gaseous phase above the solution. The amount of mercury metal in the gaseous phase will thus depend on the amount of species R reacting with the mercurous ion. The mercury in the gaseous phase may be readily determined by any of a number of well known laboratory techniques, so as to give an indirect quantitative indication of the amount of species R originally added to the solution.

The invention therefore provides a method for the quantitative determination of a chemical species capable of promoting the disproportionation of $Hg_2^{2+}$ to $Hg^{2+}$ and $Hg^\circ$ in solution, which method comprises causing the species to react with a solution comprising $Hg_2^{2+}$, to thereby produce a measurable concentration of $Hg^\circ$ in a gaseous phase above the solution, and determining the $Hg^\circ$ in the said gaseous phase.

The invention also provides apparatus for carrying out the aforesaid method, comprising a reaction vessel closed to the atmosphere for containing a solution of a mercurous compound, with a vapour space above the solution, means for introducing the said chemical species into the reaction vessel, and means for determining the amount of $Hg^\circ$ in the said vapour space.

A variety of species may be determined by the method of the invention, for example sulphite, cyanide, and chelating agents, such as aminopolycarboxylic acids, and hydroxycarboxylic acids. It is generally desirable that the value of $\beta$ for the reaction 2 above should be at least $10^8$, preferably $10^{10}$, in order that a suitable concentration of mercury should be produced in the gaseous phase although values of $\beta$ of significantly less than this, e.g. as low as $10^4$, might be satisfactory in certain circumstances. Sulphite ion is particularly amenable to determination by the method of the invention, since it forms a very strong mercury (II) complex ($\beta = 10^{24}$). Thus, the invention is capable of providing a very sensitive method for the determination of sulphite in water. This is particularly useful in effluent analysis.

Since sulphur dioxide hydrolyses in water to form sulphite ion, according to the reactions:

$$SO_2 + H_2O \rightleftharpoons H^+ + HSO_3^- \qquad (3)$$

$$HSO_3^- \rightleftharpoons H^+ + SO_3^{2-} \qquad (4)$$

the method of the invention is equally applicable to the determination of sulphur dioxide in gas mixtures, and particularly mixtures with air, such as the ambient atmosphere, and flue gas mixtures.

Since many of the reactions involved are temperature sensitive, it is most desirable that the solution should be maintained at a constant temperature throughout the determination, and the apparatus may be provided with suitable means for achieving this end, for example a water jacket or an air box surrounding the reaction vessel. Control of the temperature also enables the sensitivity and speed of response of the instrument to be varied, and it has been found that a solution temperature of from 30° to 50° C., preferably 40° C., is particularly suitable.

The solution comprising $Hg_2^{2+}$ may be a solution of any stable mercurous salt, preferably mercurous nitrate. The mercurous ion is usually provided in large excess, in comparison to the amount consumed in a single determination, so that a number of determinations can be carried out without the necessity of changing the solution. The solution is preferably made acid, in order to suppress the hydrolysis of the mercuric ion, according to the reaction $$Hg^{2+} + H_2O \longrightarrow HgO + 2H^+ \qquad (5)$$

This reaction, unless suppressed by the addition of hydrogen ions, would itself promote the disproportionation of the mercurous salt, thereby creating a high background level of mercury (O). It has been found that a dilute solution of mercurous nitrate in $10^{-3}N$ nitric acid forms a particularly suitable solution for use in the determination.

The mercury produced may be determined by any of the various available physical or chemical methods. For example, it may be determined directly in the gaseous phase, by passing the vapour to some suitable means for the detection of mercury, or instead it may be collected, and the determination carried out indirectly, for example by any of the various wet chemical methods. It is particularly desirable that vapour from the vapour space should be transported directly to some suitable means for determining mercury directly in the vapour phase, for example by atomic absorption, atomic emission or atomic fluorescence spectroscopy. Atomic absorption spectroscopy has been found to be particularly useful.

In carrying out the method of the invention, one or more standard samples will normally be used to calibrate the apparatus. Although the theory of operation of the method is described above in terms of thermodynamic equilibria, we have found that it is not necessary in order to obtain consistent readings to allow equilibrium to be reached, before carrying out the determination on the vapour. Indeed in a preferred embodiment of the invention, the solution is continuously "swept" with a carrier gas which is inert to the chemical reactions involved, the carrier gas then being passed directly to the mercury detector. A sample is then introduced into the solution and determined either as the peak height or integral of the detector signal. When this method is used for a liquid sample, the sample is preferably introduced directly into the solution, whereas gaseous samples may be introduced either into the solution or into the carrier gas stream or may replace the carrier gas. Suitable carrier gases are argon, nitrogen and $SO_2$—free air.

The carrier gas serves to separate the $Hg°$ from the solution as well as to transfer it to the mercury detector. Alternatively, no carrier gas may be used, and the vessel may be simply shaken to assist partition of $Hg°$ into the gaseous phase and the gaseous phase may then be determined by a suitable method.

In a further preferred embodiment, mercurous solution is supplied continuously at a low rate to the reaction vessel, and an equal volume of solution is continuously removed from the reaction vessel, so that the solution is continuously replenished, whilst being maintained at constant volume.

The solution used for this replenishment is preferably pre-conditioned by the passage therethrough of an inert ($SO_2$ free) gas, before it is introduced into the reaction vessel. This has the effect of lowering the blank reading and producing more reproducible results.

To this end the apparatus may be provided with a conditioning vessel for containing the solution, means for passing an inert gas through the solution in the conditioning vessel, and a conduit for passing the solution from the conditioning vessel to the reaction vessel.

The method of the invention may also be used indirectly for the determination of substances (hereinafter referred to as 'secondary' chemical species) capable of reacting with species as discussed above. For example, such substances or secondary species may be caused to react with a standard solution of a chelating agent, sulphite, or any of the other species capable of being determined according to the method of the invention, and the unreacted chelating agent or sulphite is then determined by the method of the invention, to provide a method for the determination of the said chemical substance by difference.

Figure 2:
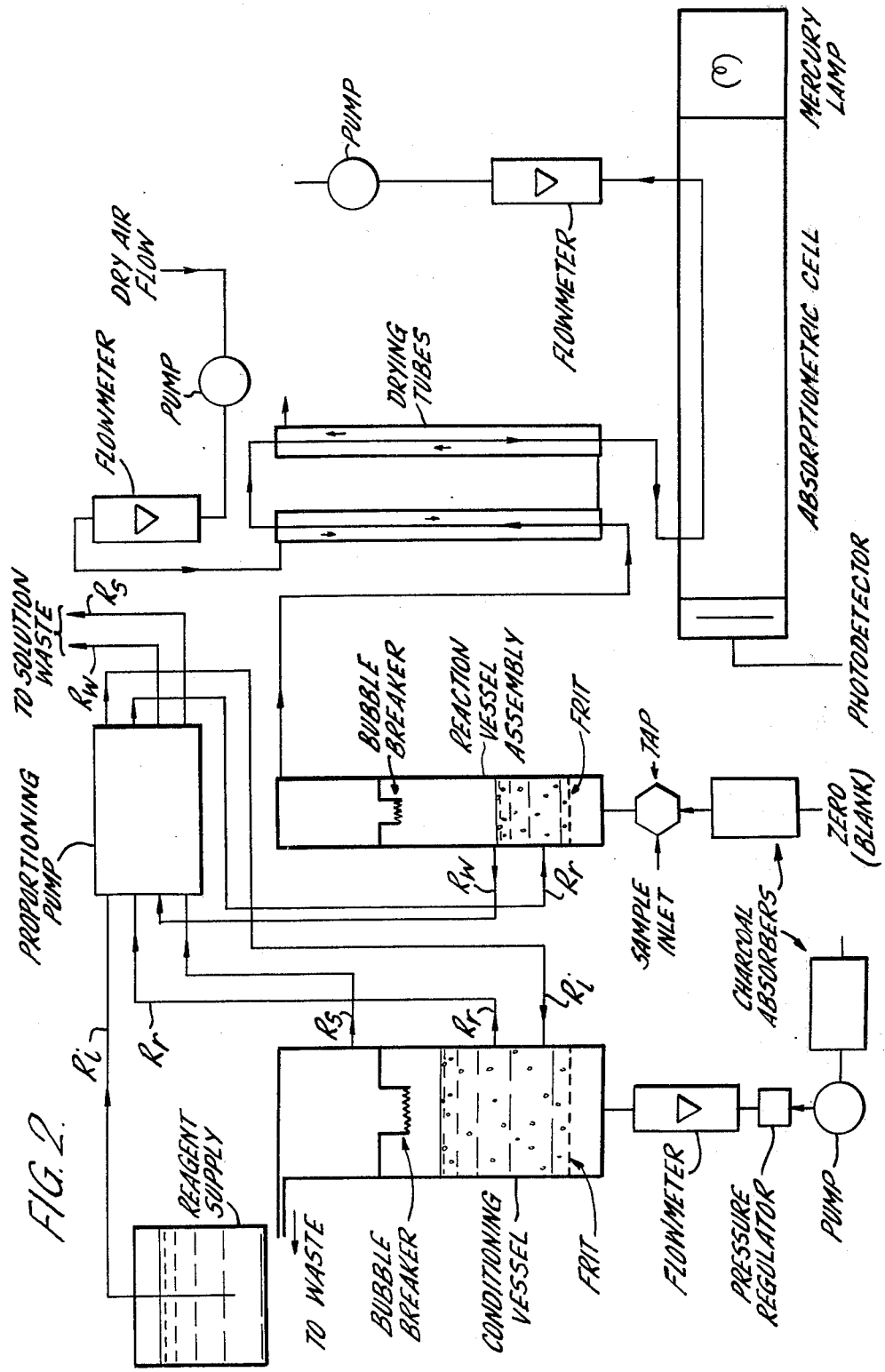
Figure 3:
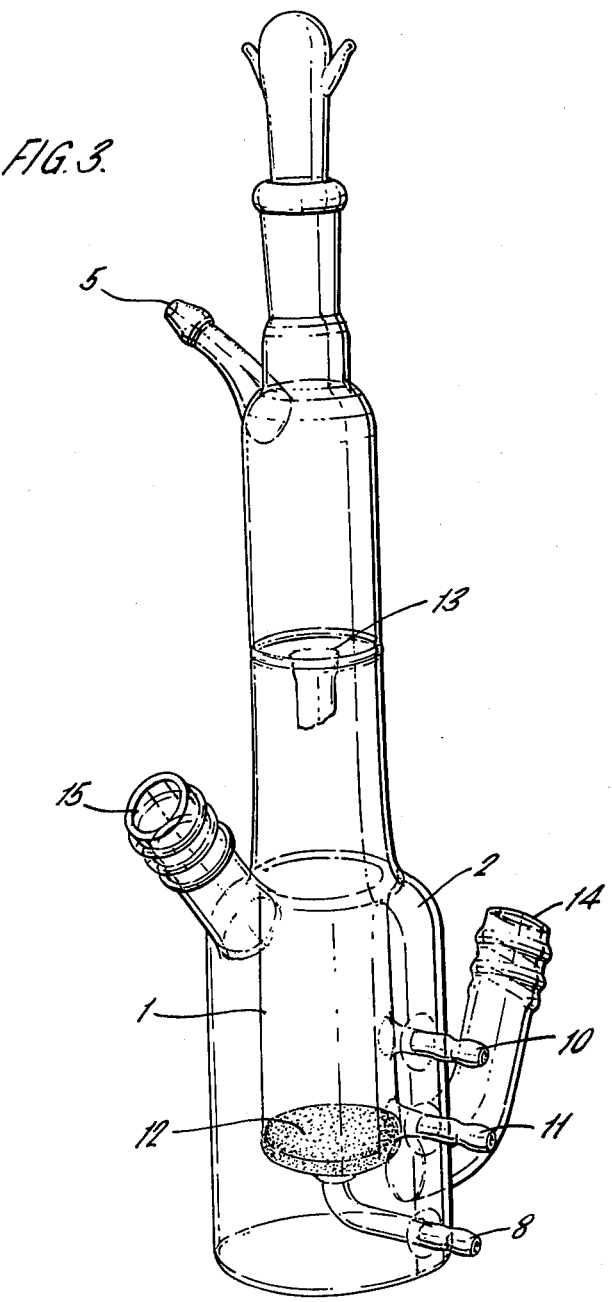

A particular embodiment of the invention will now be described with reference to the accompanying drawings in which FIG. 1 is a block schematic diagram of apparatus suitable for carrying out the method of the invention, FIG. 2 is a more detailed schematic diagram of a particular embodiment of the apparatus, and FIG. 3 shows a reaction vessel assembly suitable for use in the apparatus of FIG. 2.

In FIG. 1, a reaction chamber 1 is surrounded by a water jacket 2 through which water from a thermostatically controlled vessel 3 is supplied through lines 4. A gas outlet 5 leads from reaction vessel 1 to a mercury detector 6, in this case an atomic absorption instrument. An inlet 8 is provided at the lower part of the reaction vessel to enable gaseous samples or a carrier gas (in the analysis of liquid samples) to be bubbled through solution in the vessel, and an inlet 7 is provided in the upper part of the vessel 1 for the introduction of liquid samples.

A conditioning vessel 9 is supplied continuously with $Hg_2^{2+}$-containing solution from a reservoir. Air which has been passed over graphite or soda lime to remove $SO_2$ is bubbled continuously through solution in vessel 9, and the treated solution is pumped continuously to reaction vessel 1 through conduit 11. An equivalent amount of solution is continuously removed from reaction vessel 1 via conduit 10.

Drying tubes are incorporated into the apparatus after the reaction vessel to prevent water vapour entering the atomic absorption detector. Chemical drying tubes filled with magnesium perchlorate are efficient for this purpose but require frequent replacement. A more convenient, and preferred, form of drying tube was obtained commercially. These tubes are marketed by Perma Pure Products, and remove water selectively from the gas stream by allowing it to diffuse across a polymer membrane e.g. "Nation" copolymer membrane into a counter stream of dry air on the other side. The use of these tubes therefore, requires the addition of a pump to supply the dry air.

FIG. 2 shows a specific embodiment of suitable apparatus of which the reaction vessel assembly is shown in FIG. 3. The reaction vessel assembly of FIG. 3 is constructed of glass, and includes a reaction chamber 1 surrounded by a water jacket 2. A gaseous sample passes through the entrance port 8, through a glass frit 12, and into the reagent solution. An arrangement 13 is provided to assist in bursting bubbles and prevent droplets of solution being carried further into the system. The gas carrying the mercury vapour exits through a port 5, to the mercury detector. Water at a controlled temperature is circulated through the water jacket 2 through ports 14 and 15.

The conditioning vessel as shown in FIG. 2 differs from the reaction vessel assembly only in that it is somewhat larger, and in the addition of a solution exit port above the bubble-burst arrangement so that surplus reagent can be carried away. An $SO_2$-free carrier gas enters at the bottom, passes through a glass frit, sweeps through the reagent solution, and passes to waste through a vent at the top.

The invention is illustrated by the following examples.

EXAMPLE I

This is an example of determination carried out using apparatus generally as shown in FIG. 1, but without the conditioning vessel, the mercurous solution being stationary.

20 $\mu l$ portions of aqueous solutions containing 0.5, 1.0, 2.0 and 5.0 ng $SO_3^{2-}$ respectively were added to 5 ml of an aqueous solution containing $Hg_2^{2+}$ (nitrate) ($10^{-6}M$), in a 50 ml reaction vessel. The reaction vessel was maintained at a constant temperature of approximately 40° C. by means of a water jacket. The Hg° released was carried off in a stream of air to a mercury detector working on the principle of atomic absorption (made by Laboratory Data Control—mercury monitor model 1235). The signals from the mercury detector were registered on a chart recorder and the peak heights above the baseline were measured. A plot of peak height against ng $SO_3^{2-}$ was drawn. The within-batch standard deviations for the determination of these levels of sulphite are given in Table 1.

TABLE 1

| Standard Deviation for the Determination of Sulphite | | | | |
|---|---|---|---|---|
| Sulphite added (ng) | 0.5 | 1.0 | 2.0 | 5.0 |
| Standard deviation (ng) | 0.02 | 0.03 | 0.05 | 0.09 |

From the standard deviations, a limit of detection of less than 0.1 ng can be predicted. With 20 μl of sample, this is equivalent to a concentration of 5 $\mu g l^{-1} SO_2^{2-}$ and with 200 μl of sample is equivalent to 0.5 $\mu g l^{-1} SO_3^{2-}$. Additions of more than 500 μl sample to 5 ml of reagent solution are not normally recommended. By the use of a reaction vessel with a larger capacity it should be possible to determine lower concentrations of $SO_3^{2-}$ in larger volumes of sample.

EXAMPLE II

Using an arrangement as shown in FIG. 2, and reaction vessel as shown in FIG. 3 reagent solution is pumped at rate $R_r$ from the conditioning vessel into the reaction vessel at Port 11. A mixture of waste reagent and entrained gas is drawn by a pump from port 10, at a rate $R_w$, i.e. $R_w > R_r$ so that the reagent solution is maintained at the level of the exit port 10. Reagent is pumped from a reservoir to the lowest solution (inlet) port of the conditioning vessel, at a rate $R_i$, and from the conditioning vessel to the reaction vessel through the middle (exit) port of the conditioning vessel at a rate $R_r$. A pump connected to the highest (exit) port of the conditioning vessel takes the surplus reagent (entrained with gas) to waste at rate $R_s$. The rates are chosen such that $$R_i > R_r \text{ and } R_r + R_s > R_i$$

This arrangement ensures that the level of solution in the conditioning vessel is virtually constant at the height of the surplus exit port.

For convenience, all the pumping is done by the same multi-channel peristaltic pump. The reason for the relations between the pump rates specified above is that the performance of peristaltic pumps over long periods of continuous operation is insufficiently constant for an arrangement of balanced flows ($R_i = R_r = R_w$) to be relied on. The arrangement adopted is a precaution against flooding of the vessels with reagent solution.

Examples of suitable specific flow rates for the arrangement of FIG. 2 are as follows $R_i = 0.6$ ml min$^{-1}$ $R_r = 0.42$ ml min$^{-1}$ $R_w = 0.6$ ml min$^{-1}$ $R_s = 0.42$ ml min$^{-1}$ These rates are not necessarily optimal, but were chosen to give a convenient rate of reactant consumption.

Reagent ($10^{-6}$ mol l$^{-1}$ mercurous nitrate in $10^{-3}$ mol l$^{-1}$ nitric acid) is pumped from the reagent supply container at rate $R_i$ by the peristaltic pump to the conditioning vessel. Sulphur dioxide free air is passed through solution in the conditioning vessel to reduce the level of the blank and this air goes to waste. The conditioned reagent is passed at rate $R_r$ (via the peristaltic pump) to the reaction vessel and from here with entrained gas to waste at rate $R_w$. Any excess solution (entrained with air) is removed at rate $R_s$ from the conditioning vessel to waste.

Sample air (whose sulphur dioxide content it is desired to determine) is passed through the solution in the reaction vessel. Reaction occurs and elemental mercury is formed by the sulphite induced disproportionation of the mercurous ion. The mercury vapour is then swept out of solution by the same sample air, through the Perma tubes for drying, and into the mercury detector for measurement. A zero blank can be achieved by turning the three way tap to sample air after it has been passed through a charcoal absorber where its sulphur dioxide will be removed.

Standards containing known concentrations of $SO_2$ in air from a permeation tube calibrator are introduced to the sample inlet in place of the sample air to calibrate the instrument.

If the analyser is required to analyse for aqueous sulphite ion or other aqueous species (instead of sulphur dioxide) the reaction vessel will operate with air as a purge gas (after passing through the charcoal absorber) and the sample solution will be introduced directly into the reaction vessel (inlet port not shown).

Limits of detection as low as 0.1 p.p.b. or better of $SO_2$ in air have been found to be possible using the apparatus shown in FIG. 2.

We claim:

1. A method for the quantitative determination of a chemical species selected from the group consisting of sulphite, cyanide, sulphur dioxide, aminopolycarboxylic acids and hydroxycarboxylic acids, said species being capable of promoting the disproportionation of $Hg_2^{2+}$ to $Hg^{2+}$ and $Hg°$ in solution, which method comprises causing the species to react with a solution comprising a stable salt of $Hg_2^{2+}$ to thereby produce a measurable concentration of $Hg°$ in a gaseous phase above the solution, and determining the $Hg°$ present in the said gaseous phase.

2. A method as claimed in claim 1, wherein the said chemical species is such that the stability constant β for the reaction

wherein R is the said chemical species, has a value of at least $10^8$.

3. A method as claimed in claim 2, wherein the species is $SO_3$.

4. A method as claimed in claim 1, wherein an inert carrier gas is passed continuously through the solution and thence to a mercury detector.

5. A method as claimed in claim 4, for the determination of $SO_2$ in a mixture of gases, which method comprises introducing the gas mixture into the inert carrier gas stream or replacing the inert carrier gas stream with the said mixture of gases and observing the reaction of the mercury detector.

6. A method as claimed in claim 1, wherein the said solution is an aqueous solution of mercurous nitrate.

7. A method as claimed in claim 1, wherein the solution comprises $HNO_3$.

8. A method of determining a secondary chemical species capable of reaction with a species as defined in claim 1 which method comprises causing the secondary chemical species to react with the chemical species capable of being determined by a method as claimed in claim 1, and determining the remainder of the last mentioned species by a method as claimed in claim 1, to thereby determine the said secondary chemical species by difference.

* * * * *